United States Patent [19]

Ernst et al.

[11] Patent Number: 4,996,367
[45] Date of Patent: Feb. 26, 1991

[54] PROCESS FOR MAKING 4,4'-DIHYDROXYDIPHENYL SULFONE

[75] Inventors: Andreas B. Ernst, Glen Ellyn; Gunter Caspari, Wheaton, both of Ill.

[73] Assignee: Amoco Corporation, Chicago, Ill.

[21] Appl. No.: 453,664

[22] Filed: Dec. 20, 1989

[51] Int. Cl.$^5$ .................................. C07C 315/00
[52] U.S. Cl. ................................................ 568/33
[58] Field of Search ........................................ 568/33

[56] References Cited

U.S. PATENT DOCUMENTS

| | | | |
|---|---|---|---|
| 2,392,137 | 1/1946 | Foster | 568/33 |
| 2,833,828 | 5/1958 | Sauls | 568/33 |
| 3,065,274 | 11/1962 | Vegter et al. | 568/33 |
| 4,113,974 | 9/1978 | Mark et al. | 568/750 |
| 4,162,270 | 7/1979 | Ogata et al. | 568/33 |
| 4,382,147 | 5/1983 | Kitamura et al. | 568/33 |
| 4,820,831 | 4/1989 | Ogata et al. | 568/33 |

FOREIGN PATENT DOCUMENTS

| | | |
|---|---|---|
| 0293037 | 11/1988 | European Pat. Off. |
| 2708388 | 8/1978 | Fed. Rep. of Germany |
| 6348261 | 2/1988 | Japan |
| 2030566 | 4/1980 | United Kingdom |
| 8203857 | 11/1982 | World Int. Prop. O. |

OTHER PUBLICATIONS

Derwent Abstract of Japanese Patent 51-98239, published Aug. 1976.
J. Chem. Soc. 2854-6 (1949), S. E. Hinkel and G. H. R. Summers.
Abstract of Japanese Patent 43-24660, published May 1966.
Abstract of Japanese Patent 47-43936, published Nov. 1972.

*Primary Examiner*—Mary E. Ceperley
*Attorney, Agent, or Firm*—Reed F. Riley; William H. Magidson; Ralph C. Medhurst

[57] ABSTRACT

A process is described to make a dihydroxydiphenol sulfone product with a 4,4'-dihydroxydiphenol sulfone purity in excess of 90 wt. % by reaction of phenol and concentrated sulfuric acid in a solvent mixture containing a lower-boiling and a higher-boiling hydrocarbon, removal by azeotropic distillation of water, hydrocarbon, and phenol, phase separation of the distillate, and return of at least the phenol to the reaction at a rate which maintains a phenol to sulfuric acid mol ratio in the reaction of at least 2 to 1.

5 Claims, No Drawings

PROCESS FOR MAKING 4,4'-DIHYDROXYDIPHENYL SULFONE

BACKGROUND OF THE INVENTION

This invention relates to a batch process to prepare 4,4'-dihydroxydiphenyl sulfone from phenol and concentrated sulfuric acid and, more particularly, to a process for making a dihydroxydiphenyl product sulfone with a 4,4'-dihydroxydiphenyl sulfone isomer purity of at least 90 wt. % by reacting phenol and concentrated sulfuric acid employed in a mol ratio above 2 to 1 in a solvent mixture containing a lower-boiling and a higher-boiling hydrocarbon, removal by azeotropic distillation of water, hydrocarbon and phenol, phase separation of the distillate, and return of at least the phenol to the reaction at a rate which maintains a phenol to sulfuric acid mol ratio of at least 2 to 1.

The literature teaches that production of 4,4'-dihydroxydiphenyl sulfone generally results in crude reaction mixtures containing the desired 4,4'-dihydroxydiphenyl sulfone mixed with substantial amounts of by-product 2,4'-dihydroxydiphenyl sulfone and colored impurities. Also, that the 4,4'-isomer can be produced, but with difficulty, in an isomer yield of about 90 wt. % of the crude product, which product can be produced in about a 90 wt. % yield based upon starting material. This can be the case, for example, when the desired 4,4'-isomer is produced from starting materials comprising phenol and concentrated sulfuric acid, or phenol and p-phenolsulfonic acid. The production of a high percentage of 4,4'-isomer in the crude product and the separation of the 4,4'-isomer from admixed 2,4'-isomer heretofore has presented considerable difficulties and generally cannot be carried out in large scale operations by inexpensive preparative and separation means. For example, isomer separation can be accomplished by expensive multiple recrystallizations to obtain a high purity (99.5+) 4,4'-material. Procedures to yield a crude product containing a low percentage of the 2,2'-isomer are also complicated and costly.

It is known to prepare 4,4'-dihydroxydiphenyl sulfone by reaction of phenol and sulfuric acid (the proportion of phenol being in excess of the stoichiometric proportion of 2 mols of phenol per mol of sulfuric acid), but the desired product is usually accompanied by an unacceptably high proportion of the 2,4'-dihydroxydiphenyl sulfone isomer. In the past, various methods have been used to increase the 4,4'-isomer in the crude product as it is generally believed less expensive to produce a low amount of the 2,4'-isomer in the crude reaction product then remove it during purification of the crude product.

Japanese Patent Publication No. 51-98239 teaches reacting phenol and sulfuric acid in the presence of a solvent in which 4,4'-dihydroxydiphenyl sulfone is less soluble than the 2,4'-dihydroxydiphenyl sulfone. The solvent is gradually evaporated from the reaction system causing the 4,4'-dihydroxy isomer to separate and, since the two isomers are in equilibrium, isomerization of the 2,4'-dihydroxy isomer to the 4,4'-isomer proceeds. This method does, however, require careful control of the reaction conditions to ensure an appropriate balance between the rate of removal of the solvent and the rate of isomerization. Furthermore, the reaction product, after removal of the solvent, may be in the form of an intractable solid mass.

British Patent Application No. 2,030,566 discloses a process for the preparation of 4,4'-dihydroxydiphenyl sulfone wherein the recovered yield of 4,4'-dihydroxydiphenyl sulfone is increased by heating a mixture containing 4,4'-dihydroxydiphenyl sulfone and 2,4'-dihydroxydiphenyl sulfone in the presence of an acidic catalyst and an organic solvent. The solvent utilized in the process disclosed is o-dichlorobenzene and the catalysts utilized are organic acids or aqueous mineral acids. Dihydroxydiphenyl sulfone yields based upon starting materials from chlorinated solvents are not generally as good because the material is somewhat soluble in chlorinated solvents.

German Patent No. 2,708,388 discloses a process for preparing 4,4'-dihydroxydiphenyl sulfone by reaction of phenol with sulfuric acid in the presence of a solvent, o-dichlorobenzene, which forms an azeotrope with the water formed in the reaction. The water of reaction is removed by azeotropic distillation and the solvent is removed by distillation but the product is left as an intractable mass. The yield of the product based upon starting materials obtained by the process described is said to be 91.2% and contain less than 0.8% of the 2,4'-isomer. Because of the known solubility of the product in the solvent, special procedures have to be used to obtain a yield that high.

The presence of the by-product 2,4'-isomer, even in relatively small amounts in the purified product, greatly restricts the field of the application of the 4,4'-dihydroxydiphenyl sulfone product, particularly for polymer use. Therefore, it is of interest to reduce the amount of 2,4'-isomer in the crude product either in its preparation, purification, or both.

Another impurity made in the usual preparation processes but not often described in the literature is triphenol disulfone. This is the reaction product of three mols of phenol and two mols of sulfuric acid and is sometimes called trimer. Colored impurities are produced as well particularly in solventless processes.

One method of separating 4,4'-dihydroxydiphenyl sulfone from the 2,4'-isomer is taught in U.S. Pat. No. 3,065,274. The method of separation disclosed conducts the reaction in the presence of sym-tetrachloroethane solvent at the boiling temperature of the solvent, about 140° C. at the pressure employed. This sym-tetrachloroethane is combined with the isomer mixture to be separated, the mixture cooled to a temperature in the range of about 80° C to about 125° C., preferably about 100° C., and the solution filtered without lowering the temperature substantially, thereby obtaining a filter cake consisting of 4,4'-dihydroxydiphenyl sulfone free from substantial amounts of 2,4'-dihydroxydiphenyl sulfone. The filtrate consists essentially of sym-tetrachloroethane containing 2,4'-dihydroxydiphenyl sulfone in solution. This idea suffers from the fact that, if the system is cooled below 80° C. during or prior to filtration, the 2,4'-isomer precipitates out of solution. In addition, the product obtained by this process apparently still contains several percent of the 2,4'-isomer based on the melting point given. Also, the sym-tetrachloroethane can react to a small extent with sulfuric acid, resulting in other types of impurities in the product.

European Patent Application 0293037 to AKZO N.V. teaches the preparation of the 4,4'-isomer by reaction of phenol with sulfuric acid in the presence of a suspending agent such as Isopar H, and an azeotroping agent such as Isopar E, wherein 2-3 mols of phenol per mol of sulfuric acid may be used, but a 1-10% excess of phenol is preferred. The crude product is said to contain greater than 95% 4,4'-isomer which it is alleged may be recrystallized in a single step to a product containing greater than 99.5% of the 4,4'-isomer. No examples of the recrystallization or any recrystallization solvents are given.

Now it has been found that, when two hydrocarbons such as Isopar H and E are used as a mixed solvent in the reaction of phenol and sulfuric acid and the reaction mixture azeotropically distilled, the vapor taken overhead when condensed can form three immiscible layers, the densest layer of which is mostly phenol with a smaller amount of water. Separation and return of this densest layer provides a convenient and economic way to return phenol to the reaction mixture to keep the phenol in the stoichiometric ratio or in slight excess during the reaction, as a proper phenol to sulfuric acid ratio is required for the preparation of a product having the optimal isomeric as well as colored product purity. Such a process conveniently makes a crude dihydroxydiphenol sulfone product in over 95 wt % with a 4,4'-isomer content greater than 90 wt %, a product which can be easily recrystallized from water to form a greater than 99 wt % 4,4'-isomer product.

SUMMARY OF THE INVENTION

The invention contained herein is a batch process to produce a dihydroxydiphenol sulfone product from phenol and sulfuric acid in greater than 95 wt % yield based upon said sulfuric acid, said product containing at least 90 wt % of the 4,4'-dihydroxydiphenyl sulfone isomer comprising:

reaction of said sulfuric acid and said phenol in an organic solvent mixture containing a lower-boiling and a higher-boiling hydrocarbon, said phenol and said sulfuric acid and being employed in a mol ratio of above 2 to 1;

removal of reaction-produced water, hydrocarbon, and phenol, from said reaction by azeotropic distillation and the formation of a condensed phase therefrom which is separable into at least two immiscible layers; one layer of which is rich in phenol; and return of at least the rich-in-phenol layer to said reaction at a rate which keeps the mol ratio of phenol to sulfuric acid in the reaction at least 2 to 1.

DETAILED DESCRIPTION OF THE INVENTION

The feeds to the process described herein are phenol and concentrated sulfuric acid. By concentrated sulfuric acid is meant a solution greater than about 80 wt %, more preferably greater than about 90 wt %, and most preferably greater than about 95 wt % $H_2SO_4$. The phenol is used in a 2 to about 2.5, phenol to $H_2SO_4$ mol ratio, more preferably in a 2 to about 2.25 mol ratio, and most preferably, in a 2 to about 2.1 mol ratio. The phenol to sulfuric acid ratio is critical to product purity, as too much phenol can produce additional trimer and too little phenol can produce colored products and increased amounts of the 2,4'-isomer.

It is advantageous to add the concentrated sulfuric acid slowly over a period of time to the phenol dissolved in the mixed hydrocarbon solvent. The sulfuric acid is added to the mixed solvent containing phenol at or below the reflux temperature of the reaction mixture, and the temperature is gradually raised as the overhead is removed and condensed to allow the immiscible phases to settle. A beginning temperature of about 100 to about 140° C. and a final temperature of about 160 to about 190° C., depending upon the hydrocarbons used are usual.

The lower-boiling hydrocarbon is an inert material boiling at a temperature or in a temperature range in the temperature range between about 70 and about 140° C., more preferably, between about 100 and about 130° C. A useful material is Isopar E, octane, isooctane, cyclohexane, methylcyclohexane, chlorobenzene, o-dichlorobenzene, and the like; Isopar E is the preferred lower-boiling hydrocarbon.

The higher-boiling hydrocarbon is an inert material boiling at a temperature or in a temperature range in the temperature range between about 160 and about 220° C., more preferably between about 170 and about 190° C. Such a material is Isopar H, decane, dodecane, decalin, and the like; Isopar H is the preferred higher-boiling hydrocarbon.

The lower-boiling and higher-boiling hydrocarbons are generally mixed in proportions such that the higher-boiling hydrocarbon is present in substantially greater amount. Greater than about a 3 to 1 weight excess is preferred, and greater than about an 8 to 1 weight excess is more preferred.

As the reaction between phenol and sulfuric acid proceeds in the refluxing mixed solvent, water of reaction, phenol, and hydrocarbon (essentially all lower-boiling hydrocarbon) are slowly removed as overhead. The overhead, when condensed and allowed to settle, forms at least two layers (three with a mixture of Isopar H and Isopar E). One of the layers is essentially a phenol-rich, water-in-phenol phase. This phase, generally the densest of the condensed phases, is conveniently returned to the reaction, and it is returned at a rate designed to keep the phenol to sulfuric acid mol ratio in the reaction 2 to 1 or greater. This is necessary as phenol is both used up in the reaction and lost in the overhead which reduces the phenol in the reaction to a point favoring production of various impurities, such as increased 2,4'-isomer, colored impurities, and trimer.

During the reaction, both 4,4'-dihydroxydiphenyl sulfone and the 2,4'-isomer are formed, but the 2,4'-isomer can convert to the 4,4'-isomer at the reflux temperature, particularly in the presence of a 2 to 1 or greater phenol to sulfuric acid mol ratio.

The crude dihydroxydiphenyl sulfone product is produced in an about 95 wt % yield, more preferably, in an about a 97 wt % yield, based on sulfuric acid. The 4,4'-isomer content of the crude product is preferably more than about 92 wt %, and, more preferably, more than about 95 wt %.

The crude product generally contains less than about 2 wt % of trimer, more preferably, less than about 1 wt % of trimer. Colored impurities can be conveniently monitored by determining the absorbance, A, in methanol of 5 wt % solutions using a 50 mm cell. An absorbance in the crude product of less than about 0.7 is desired; more preferably, less than about 0.5, and most preferably, an absorbance less than about 0.35 is desirable.

The crude dihydroxydiphenyl sulfone product may be purified from 2,4'-isomer, trimer and colored impurities by a number of different techniques which have been reported in the literature. One method involves recrystallization from water or dilute base and treatment with a carbonaceous adsorbent.

The following Examples will serve to illustrate certain embodiments of the herein disclosed invention. These Examples should not, however, be construed as limiting the scope of the novel invention as they are many variations which may be made thereon without departing from the spirit of the disclosed invention, as those of skill in the art will recognize.

EXAMPLES

General

Isomer content including determination of triphenol disulfone (trimer) in a crude product mixture was determined by high-performance liquid chromotography (HPLC).

The bisphenol-S was analyzed by an external standards HPLC method using a acetonitrile/water (0.1% formic acid) mobile phase and a 5 μm Spherisorb ODS II, 250×4.6 mm column. A UV detector set at 254 nm was used as a detection system with an integrator for peak quantitation. A standard sample of bisphenol-S was analyzed by quantitative silation gas liquid chromatography for weight percent concentration of the 2,4'-isomer and trimer concentrations. This sample was used to calibrate the HPLC for the external standards method. For analysis, a 10.0 mg sample of bisphenol-S was weighed out and diluted to 10 ml with mobile phase. A 10 μl injection was made to the HPLC system via a closed loop autosampler and the material analyzed for 2,4'-isomer and trimer content. The balance of the material was taken to be 4,4'-isomer.

Color was determined by determining the absorbance at 475 nm in a 50 mm silica cell for a 5.0 wt % solution in methanol using the formula A =log (Po/P) =abc in which a is molar absorptivity, b is path length in cm, and c is molar concentration.

COMPARATIVE EXAMPLE 1

Sulfuric acid (102.5 g, 95.7% 1.0 mol) was added dropwise at 100° C. within 15 min to a solution of 198 g (2.10 mol) of phenol in 330 g of a Isopar H, supplied by Exxon Co. USA, and 32 g of a Isopar E, supplied by Exxon Co. USA, kept in a 1 L resin kettle. The kettle was equipped with a nitrogen inlet tube, a thermometer, a condenser attached to a Barrett type moisture test receiver, and an overhead stirrer. The reaction was heated stepwise to 170° C. and was kept at 170° C. for 2 hr. At 150° C., water began to azeotrope into the Barrett receiver where three immiscible liquid phases formed. The volume of the two denser liquid phases which contain large amounts of phenol (lower layer, 70% phenol at 25° C; middle layer, 8% phenol at 25° C.) and the amount of phenol in the two phases, during the reaction is shown in Table 1 below. The phenol layer in the condensed overhead was not returned to the reaction.

TABLE 1

| Reaction Temp °C. | Reaction Time (min) | Lower Layer ml | Middle Layer ml | Phenol in Lower Layer (g)[1] | Phenol in Middle Layer (g)[2] | Overhead Phenol as % of Overcharge (%)[3] |
|---|---|---|---|---|---|---|
| 130 | 20 | — | — | — | — | — |
| 150 | 55 | 3 | 16 | 2.2 | 1.3 | 33.7 |
| 160 | 95 | 8 | 22 | 5.8 | 1.8 | 77.6 |
| 165 | 120 | 11 | 28 | 7.9 | 2.2 | 103.1 |
| 170 | 155 | 18 | 32 | 12.9 | 2.6 | 158.2 |

TABLE 1-continued

| Reaction Temp °C. | Reaction Time (min) | Lower Layer ml | Middle Layer ml | Phenol in Lower Layer (g)[1] | Phenol in Middle Layer (g)[2] | Overhead Phenol as % of Overcharge (%)[3] |
|---|---|---|---|---|---|---|
| 170 | 245 | 18 | 36 | 12.9 | 2.9 | 161.2 |

[1]Lower phase: 70% phenol at 25° C.; density at 25° C., 1.027
[2]Middle phase: 8% phenol at 25° C.; density at 25° C., 0.991
[3]Total phenol charge: 198 g (2.10 mols)
Stoichiometric phenol charge: 188.2 g (2.0 mols)
Phenol overcharge: 9.8 g (0.10 mols)

The reaction mixture was then cooled to 100° C. and filtered. The filter cake was resuspended in hexane, filtered, and dried overnight in a vacuum oven yielding 209.0 g (83.5% based on sulfuric acid) which contains 93.3% of the 4,4'-isomer, 5,3% of the 2,4'isomer, and 1.4% of triphenol disulfone (trimer).

Absorbance of the product at 475 nm made up as a 5.0 wt. % solution in methanol in a 50 mm cell was 1.379.

EXAMPLE 2

The procedure of Example 1 was repeated with 102.5 g of 95.7% sulfuric acid added to 198 g (2.10 mols) of phenol in 330 g of Isopar H and 32 g of Isopar E. The densest layer in the overhead receiver was returned to the reaction mixture. The amount of phenol in the overhead system during the reaction is shown in Table 2 below.

TABLE 2

| Reaction Temp °C. | Reaction Time (min) | Lower Layer ml | Middle Layer ml | Phenol in Lower Layer (g)[1] | Phenol in Middle Layer (g)[2] | Overhead Phenol as % of Overcharge (%)[3] |
|---|---|---|---|---|---|---|
| 130 | 15 | — | — | — | — | — |
| 150 | 55 | 3 | 18 | 2.2 | 1.4 | 36.7 |
| 160 | 95 | 7 | 25 | 5.0 | 2.0 | 71.4 |
| 165 | 120 | 10 | 29 | 7.2 | 2.3 | 96.9 |
| 10 ml of the lower layer was returned | | | | | | |
| 170 | 145 | 8 | 35 | 5.8 | 2.8 | 87.8 |
| 8 ml of the lower layer was returned | | | | | | |
| 170 | 175 | 6 | 38 | 4.3 | 3.0 | 74.5 |
| 6 ml of the lower layer was returned | | | | | | |
| 170 | 205 | 2 | 39 | 1.4 | 3.1 | 45.9 |
| 2 ml of the lower layer was returned | | | | | | |
| 170 | 250 | 0.5 | 39 | 0.4 | 3.1 | 35.7 |

[1]Lower phase: 70% phenol at 25° C.; density at 25° C. is 1.027
[2]Middle phase: 8% phenol at 25° C.; density at 25° C. is 0.991
[3]Total phenol charge: 198 g (2.10 mols)
Stoichiometric phenol charge: 188.2 g (2.0 mols)
Phenol overcharge: 9.8 g (0.10 mols)

The reaction mixture was filtered at 100° C., the filter cake resuspended in hexane, filtered, and dried in a vacuum oven.

Total yield was 245 g (97.9% based on sulfuric acid) which was 94.0 wt. % of 4,4'-isomer, 5.0 wt. % of 2,4'-isomer, and 1.1 wt. % of trimer.

Absorbance of the product at 475 nm made up as a 5.0 wt. % solution in methanol in a 50 mm cell was 0.158.

Comparative Example 3

Sulfuric acid (50.8 g, 96.4%, 0.5 mol) was added to phenol (94.1 g, 1.00 mol) in 43 g of o-dichlorobenzene (o-DCB) as both suspending agent and azeotroping agent at 130° C. The reaction mixture was heated stepwise to 185° C. Throughout the course of the reaction, the azeotroped water, o-dichlorobenzene, and phenol were removed, condensed, and the lower layer of o-DCB and phenol returned to the reactor. At the end of the reaction, 445.g of o-DCB was added for dilution and a temperature of 120° C reached. The solids were collected on a filter and suspended twice at 110° C. in 200 g of o-DCB each. After a hexane wash to remove o-DCB the product was vacuum oven dried and analyzed by HPLC and by visible absorbance. Table 3 below summarizes the results of several runs with varying starting mol ratios of phenol to sulfuric acid obtained.

TABLE 3

| Mols PhOH/ $H_2SO_4$ | Hr at 185° C. | Total Yield[1] (%) | Product Composition | | | Color[2] |
|---|---|---|---|---|---|---|
| | | | 4,4'- (%) | 2,4'- (%) | Trimer (%) | |
| 2.0 | 1.5 | 76.9 | 93.87 | 5.87 | 0.26 | 1.387 |
| 2.0 | 3.0 | 77.6 | 94.22 | 5.47 | 0.31 | 1.426 |
| 2.1 | 1.5 | 78.8 | 97.28 | 2.23 | 0.49 | 0.269 |
| 2.1 | 3.0 | 81.4 | 97.58 | 2.32 | 0.10 | 0.382 |
| 2.2 | 3.0 | 82.2 | 97.58 | 2.24 | 0.18 | 0.345 |

[1]Wt % based on sulfuric acid.
[2]Absorbance at 475 nm of 5.0% methanol solutions measured in 50 mm cells.

What is claimed is:

1. A batch process to produce a dihydroxydiphenyl sulfone product from phenol and concentrated sulfuric acid in greater than 95 wt. % yield based upon said sulfuric acid, said product containing at least 90 wt. % of the 4,4'-dihydroxydiphenyl sulfone isomer, comprising:
    reaction of said sulfuric acid and said phenol in an organic solvent mixture containing a lower-boiling and a higher-boiling hydrocarbon, said phenol and said sulfuric acid being employed in a mol ratio of about 2 to 1;
    removal of reaction-produced water, hydrocarbon, and phenol from said reaction by azeotropic distillation and the formation of a condensed phase therefrom which separates into at least two immiscible layers, one layer of which is rich in phenol; and
    return of at least the rich-in-phenol layer to said reaction at a rate which keeps the mol ratio of phenol to sulfuric acid in the reaction at least 2 to 1.

2. The process of claim 1 wherein said lower-boiling hydrocarbon is selected from the group consisting of Isopar E, octane, isooctane, cyclohexane, methylcyclohexane, chlorobenzene, and dichlorobenzene, and said higherboiling hydrocarbon is selected from the group consisting of Isopar H, dodecane, decalin, and decane.

3. The process of claim 1 wherein said lower and higher-boiling hydrocarbons are Isopar E and Isopar H respectively.

4. The process of claim 3 wherein said condensed phase separates into three immiscible layers, the densest layer containing a major amount of phenol and a minor amount of water, and the which said densest layer is returned to said reaction at a rate which keeps the mol ratio of phenol to sulfuric acid in the reaction at least 2 to 1.

5. The process of claim 4 wherein said yield based upon said sulfuric acid is greater than 97 mol % and said product contains at least 96 wt. % of the 4,4'-dihydroxydiphenyl sulfone isomer.

* * * * *

UNITED STATES PATENT AND TRADEMARK OFFICE
CERTIFICATE OF CORRECTION

PATENT NO.   : 4,996,367

DATED        : February 26, 1991

INVENTOR(S)  : Andreas B. Ernst, Gunter Caspari

It is certified that error appears in the above-identified patent and that said Letters Patent is hereby corrected as shown below:

```
LOCATION—LINE
ABSTRACT  1       "dihydroxydiphenol" should read --dihydroxydiphenyl--
ABSTRACT  2       "4,4'-dihydroxydiphenol" should read --4,4'dihydroxydiphenyl--
Col. 1    41-42   "2,2'-isomer" should read --2,4'-isomer--
     2    23      "contain" should read --contains--
     3    21-22   "dihydroxydiphenol" should read --dihydroxydiphenyl--
     3    29      "dihydroxydiphenol" should read --dihydroxydiphenyl--
     7    3       "445.g" should read --445 g--
     8    16      "higherboiling" should read --higher-boiling--
     8    24      "and the" should read --and in--
```

Signed and Sealed this

Twenty-fifth Day of August, 1992

Attest:

DOUGLAS B. COMER

Attesting Officer        Acting Commissioner of Patents and Trademarks